United States Patent
Kogure

(10) Patent No.: US 6,618,661 B2
(45) Date of Patent: Sep. 9, 2003

(54) ROAD FRICTION COEFFICIENTS ESTIMATING APPARATUS FOR VEHICLE

(75) Inventor: Masaru Kogure, Tokyo (JP)

(73) Assignee: Fuji Jukogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/984,425

(22) Filed: Oct. 30, 2001

(65) Prior Publication Data

US 2002/0072842 A1 Jun. 13, 2002

(30) Foreign Application Priority Data

Oct. 31, 2000 (JP) ........................... 2000-332387

(51) Int. Cl.$^7$ .............. B61C 15/08; B62D 5/04; B60T 8/24
(52) U.S. Cl. ................ 701/80; 701/72; 180/410
(58) Field of Search ............... 701/80, 41, 70, 701/72, 78, 83, 44, 73; 180/410, 422, 446, 233, 197, 247, 248; 303/140, 146, 148, 149

(56) References Cited

U.S. PATENT DOCUMENTS

| | | | |
|---|---|---|---|
| 5,450,919 A | * 9/1995 | Shitani | 180/233 |
| 5,519,614 A | * 5/1996 | Miichi et al. | 364/424.05 |
| 5,742,917 A | 4/1998 | Matsuno | 701/69 |
| 6,035,251 A | * 3/2000 | Hac et al. | 701/70 |
| 6,091,214 A | * 7/2000 | Yamawaki et al. | 318/52 |
| 6,239,568 B1 | * 5/2001 | Sugitani et al. | 318/466 |

FOREIGN PATENT DOCUMENTS

| | | |
|---|---|---|
| EP | 0 444 772 A2 | 9/1991 |
| EP | 1 072 490 A2 | 1/2001 |
| JP | 2000-039289 | 2/2001 |

OTHER PUBLICATIONS

European Search Report dated Feb. 19, 2002.

* cited by examiner

Primary Examiner—Tan Q. Nguyen
Assistant Examiner—Dalena Tran
(74) Attorney, Agent, or Firm—McGinn & Gibb, PLLC

(57) ABSTRACT

A road friction coefficient estimating apparatus for a vehicle includes a high friction coefficient road reference value estimating section for calculating a high friction coefficient road reference yaw rate based on a vehicle motion model when the vehicle travels on a road surface with high friction coefficient, an actual value estimating section for calculating an actual yaw rate, a Lissajou figure processing section for forming a Lissajou's figure based on the high friction coefficient road reference yaw rate and the actual yaw rate and for calculating a gradient and area of this Lissajou's figure, a road friction coefficient estimating section for estimating a road friction coefficient based on the area of the Lissajou's figure when the gradient is in the neighborhood of 45 degrees and for estimating a road friction coefficient based on a lateral acceleration when the gradient is out of the neighborhood of 45 degrees.

13 Claims, 7 Drawing Sheets

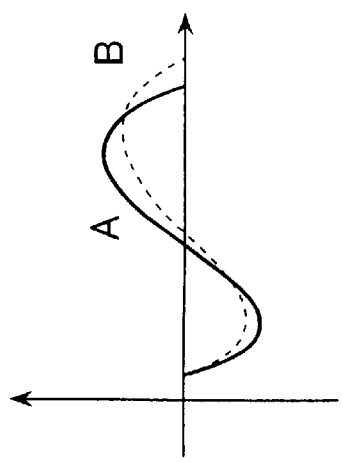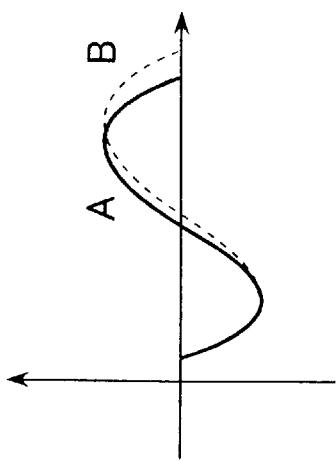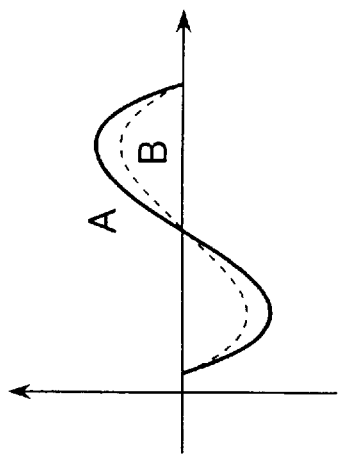
FIG.8a
FIG.8b
FIG.8c
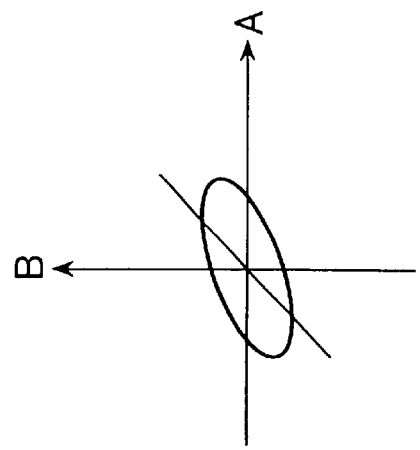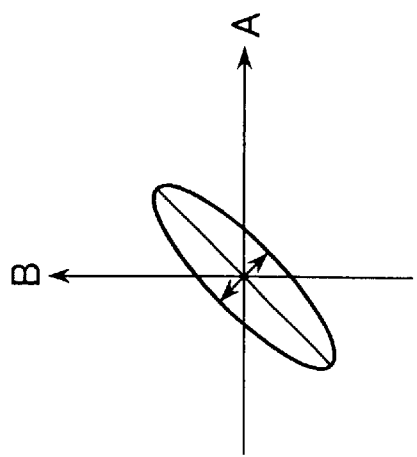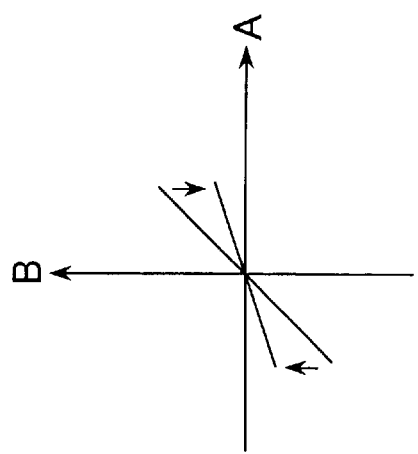
AREA SIZE : NO CHANGE
DELAY BETWEEN WAVEFORMS : YES
AREA SIZE : REDUCED
DELAY BETWEEN WAVEFORMS : NO
AREA SIZE : CHANGED
DELAY BETWEEN WAVEFORMS : YES

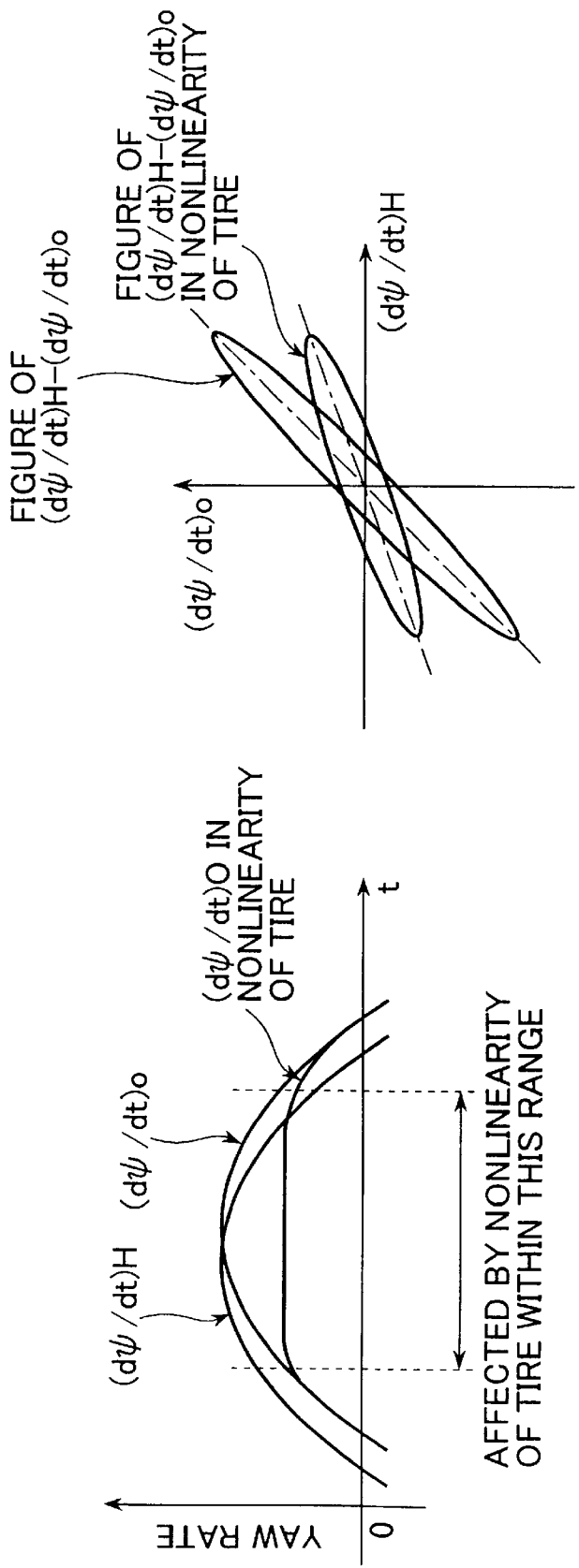

ROAD FRICTION COEFFICIENTS ESTIMATING APPARATUS FOR VEHICLE

BACKGROUND OF THE INVENTION

1. Field of the Invention

The present invention relates to a road friction coefficients estimating apparatus for a vehicle for estimating friction coefficients on road surfaces and more particularly to a road friction coefficients estimating apparatus capable of accurately estimating friction coefficients on road surfaces by a simple method using vehicle motion parameters such as lateral acceleration, yaw rate and the like.

2. Discussion of Prior Arts

In recent years, numerous vehicle control technologies such as traction control technologies, braking force control technologies, torque distribution control technologies and the like, have been proposed and some of these control technologies have been realized in actual automobile markets. Many of these control technologies use friction coefficients on road surfaces (hereinafter, referred to as "road friction coefficient") for calculation or correction of control parameters. Accordingly, in order to execute the control properly, it is necessary to estimate accurate road friction coefficients.

Several technologies in which road friction coefficients are estimated based on vehicle motion parameters such as lateral acceleration, yaw rate have been proposed. For example, the applicant of the present invention proposes a technology in which road friction coefficients are estimated based on the comparison of an actual yaw rate estimated from an observer with a yaw rate calculated using a vehicle motion model on a high friction coefficient road surface and a yaw rate calculated using a vehicle motion model on a low friction coefficient road surface respectively in Japanese Patent Application No. Toku-Gan-Hei 11-217508.

However, since the above technology needs two vehicle motion models, high and low friction coefficient road surface models, the technology has a disadvantage of taking much time for tuning. Particularly, in case of the low friction coefficient road surface model, it is necessary to take a nonlinearity of tire into consideration and therefore the vehicle motion model becomes complicated and this is a primary cause of taking much time for tuning. Further, since the above technology is constituted by two vehicle motion models, the technology has a defect of complicated logic and large amount of calculations.

SUMMARY OF THE INVENTION

It is an object of the present invention to provide a vehicular road friction coefficient estimating apparatus having a simple construction and a small amount of calculations and capable of easily making a tuning and estimating stable and accurate road friction coefficients over broad traveling conditions.

The road friction coefficient estimating apparatus for a vehicle comprises an actual value estimating means for estimating an actual value of a vehicle motion parameter, a high friction coefficient road reference value estimating means for estimating a high friction coefficient road reference value of the vehicle motion parameter based on a vehicle motion model when the vehicle travels on a road surface with high friction coefficient and a road friction coefficient estimating means for forming a Lissajou's figure based on the actual value and the high friction coefficient road reference value and for estimating a road friction coefficient according to an area of the Lissajou's figure when a gradient of the Lissajou's figure is in the neighborhood of 45 degrees and for estimating a road friction coefficient according to a lateral acceleration of the vehicle when the gradient is in a range out of the neighborhood of 45 degrees.

DESCRIPTION OF THE DRAWINGS

FIGS. 8a to 8c are explanatory views showing various Lissajou's figures drawn by two waveforms;

FIG. 9a is an explanatory view showing an effect of nonlinearity of tire;

FIG. 9b is an explanatory view showing an effect of nonlinearity of tire; and

DETAILED DESCRIPTION OF PREFERRED EMBODIMENTS

Figure 1:
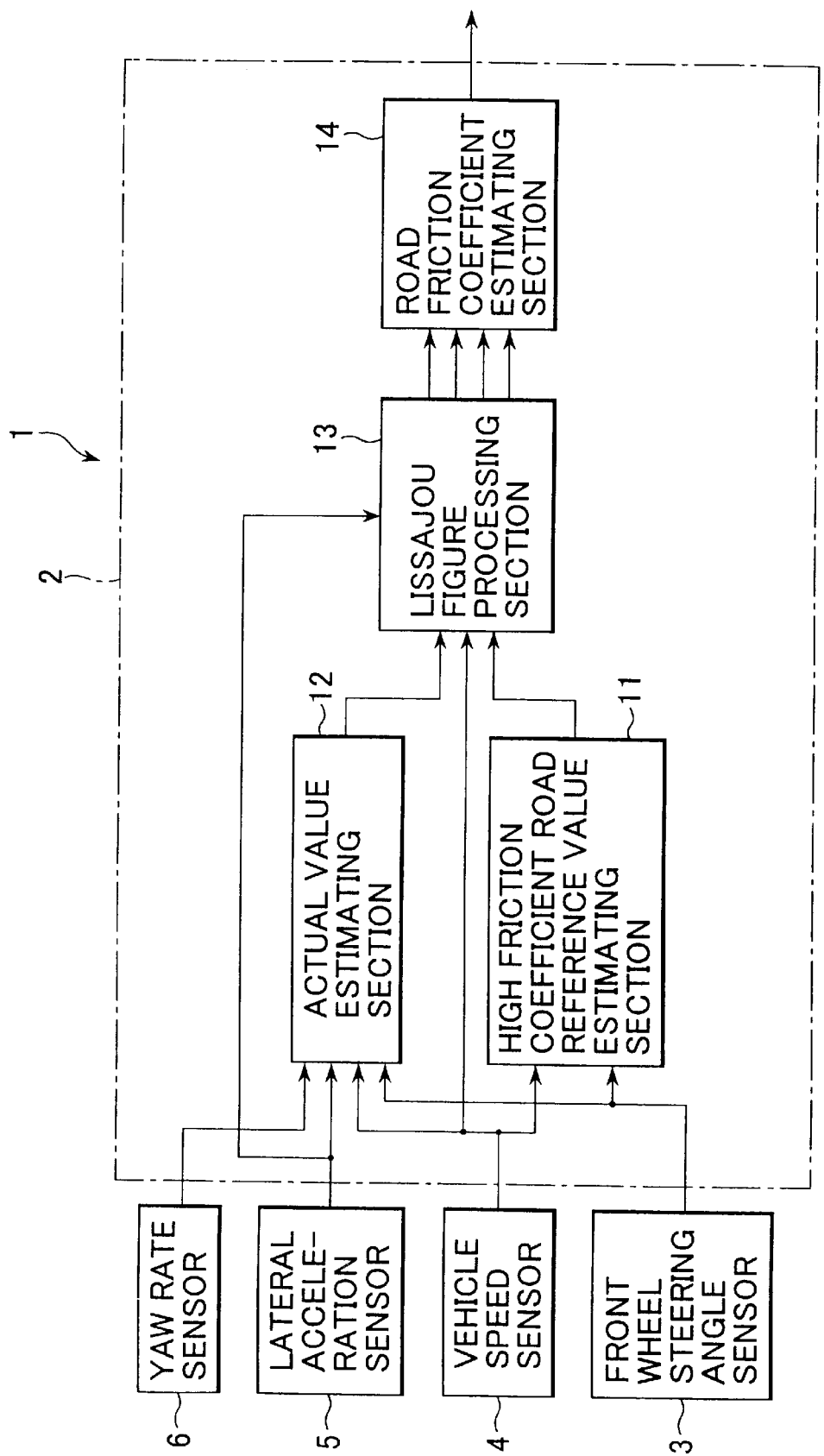
FIG. 1 is a functional block diagram showing a road friction coefficient estimating apparatus according to an embodiment of the present invention.

Referring now to FIG. 1, reference numeral 1 denotes a road friction coefficient estimating apparatus mounted on a vehicle for estimating road friction coefficients and reference numeral 2 denotes a control section of the road friction coefficient estimating apparatus 1. The control section 2 is connected with a front wheel steering angle sensor 3, a vehicle speed sensor 4, a lateral acceleration sensor 5 and a yaw rate sensor 6 and inputs signals of front wheel steering angles $\delta_{fs}$, vehicle speed $V_s$, lateral acceleration $(d^2y/dt^2)_s$, yaw rate $(d\phi/dt)_s$, (yaw angular velocity) from respective sensors. A subscript "$_s$" is for indicating a value arisen from a sensor.

The control section 2 estimates and outputs road friction coefficients. The control section 2 comprises a high friction coefficient road reference value estimating section 11, an actual value estimating section 12, a Lissajou figure processing section 13 and a road friction coefficient estimating section 14.

The high friction coefficient road reference value estimating section 11 inputs vehicle speed $V_s$ and front wheel steering angle $\delta_{fs}$, calculates high friction coefficient road reference yaw rate $(d\phi/dt)_H$ corresponding to the detected vehicle speed $V_s$ and front wheel steering angle $\delta_{fs}$ according to a vehicle motion model on the basis of an equation of vehicle motion on a road surface with high friction coefficient and outputs the high friction coefficient road reference yaw rate $(d\phi/dt)_H$ to the Lissajou figure processing section 13. Further, the high friction coefficient road reference value estimating section 11 outputs yaw rate $(d^2\phi/dt^2)_s$ besides the high friction coefficient road reference yaw rate $(d\phi/dt)_H$ to the Lissajou figure processing section 13. The subscript "$_H$" of parameters outputted from the high friction coefficient road reference value estimating section 11 denotes high friction coefficient road reference related parameters.

Figure 2:
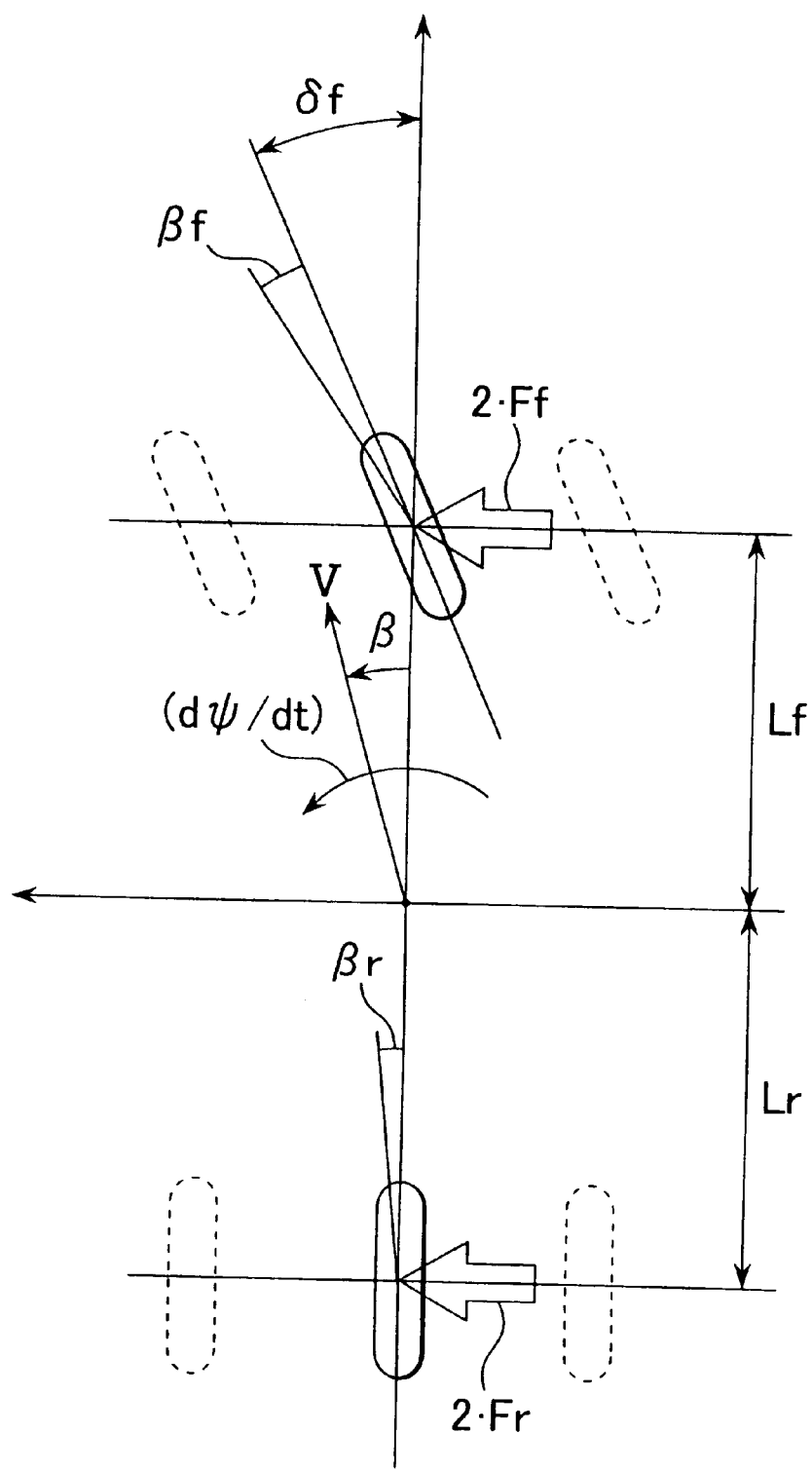
FIG. 2 is a diagram showing a two wheel vehicle model equivalent to a four wheel vehicle.

A vehicle motion model used in the high friction coefficient road reference value estimating section 11 and the calculation of parameters will be described by reference to FIG. 2. The equation of lateral transitional motion of a vehicle is expressed using the vehicle motion model illustrated in FIG. 2 as:

$$M \cdot (d^2y/dt^2) = 2 \cdot F_f + 2 \cdot F_r \quad (1)$$

where M is mass of a vehicle; $F_f$, $F_r$ are cornering forces of front and rear wheels, respectively; and $d^2y/dt^2$ is lateral acceleration.

On the other hand, the equation of rotational motion around gravity center of the vehicle is expressed as:

$$I_z \cdot (d^2\phi/dt^2) = 2 \cdot F_f L_f - 2 \cdot F_r \cdot L_r \quad (2)$$

where $I_z$ is yaw moment of inertia of the vehicle; $L_f$, $L_r$ are distances from the center of gravity to the front and rear wheels, respectively; and $(d^2\phi/dt^2)$ is yaw angular acceleration.

Further, the lateral acceleration $(d^2y/dt^2)$ is expressed as:

$$(d^2y/dt^2) = V \cdot ((d\beta/dt) + (d\phi/dt)) \quad (3)$$

where V is vehicle speed; $\beta$ is slip angle of a vehicle; and $(d\beta/dt)$ is slip angular velocity of a vehicle.

The cornering forces have a response similar to a first-order time lag. In this case, this time lag being neglected and letting the cornering forces be linearized introducing an idea of equivalent cornering power in which suspension characteristic is involved in tire characteristic, the cornering forces are expressed as follows:

$$F_f = -K_f \beta_f \quad (4)$$

$$F_r = -K_r \cdot \beta_r \quad (5)$$

where $K_f$, $K_r$ are equivalent cornering powers of front and rear wheels, respectively; and $\beta_f$, $\beta_r$ are lateral slip angles of front and rear wheels, respectively.

Using equivalent cornering powers and taking the effect of roll and suspension of the vehicle into consideration, lateral slip angles $\beta_f$, $\beta_r$ are can be simplified as follows:

$$\beta_f = \beta + L_f (d\phi/dt)/V - \delta_f \quad (6)$$

$$\beta_r = \beta - L_r \cdot (d\phi/dt)/V \quad (7)$$

where $\delta_f$ is steering angle of front wheel.

The following equation of state is obtained from the aforesaid equations of motion:

$$(dx(t)/dt) = A \cdot x(t) + B \cdot u(t) \quad (8)$$

$$x(t) = [\beta (d\phi/dt)]^T$$

$$u(t) = [\delta_f 0]^T$$

$$A = \begin{bmatrix} a_{11} & a_{12} \\ a_{21} & a_{22} \end{bmatrix}$$

$$B = \begin{bmatrix} b_{11} & b_{12} \\ b_{21} & b_{22} \end{bmatrix}$$

$$a_{11} = -2 \cdot (K_f + K_r)/(M \cdot V)$$

$$a_{12} = -1 - 2 \cdot (L_f \cdot K_f - L_r \cdot K_r)/(M \cdot V^2)$$

$$a_{21} = -2 \cdot (L_f K_f - L_r \cdot K_r)/I_z$$

$$a_{22} = -2 \cdot (L_f^2 \cdot K_f + L_r^2 \cdot K_r)/(I_z \cdot V)$$

$$b_{11} = 2 \cdot K_f/(M \cdot V)$$

$$b_{21} = 2 \cdot L_f K_f/I_z$$

$$b_{12} = b_{22} = 0$$

In the high friction coefficient road reference value estimating section 11, a high friction coefficient road reference based slip angular velocity $(d\beta/dt)_H$ and a refernce road based yaw angular acceleration $(d^2\phi/dt^2)_H$ are obtained by calculating $(dx(t)/dt) = [(d\beta/dt) \ (d^2\phi/dt^2)]^T$ in a vehicle operating condition (vehicle speed V, front wheel steering angle $\delta_f$), when equivalent cornering powers $K_f$, $K_r$ at 1.0 for example of road friction coefficient have been established beforehand in the formula (8). Then, a high friction coefficient road reference vehicle slip angle $\beta_H$ and a high friction coefficient road reference yaw rate $(d\phi/dt)_H$ are obtained by integrating the vehicle slip angular velocity $(d\beta/dt)_H$ and the yaw angular acceleration $(d^2\phi/dt^2)_H$.

The actual value estimating section 12 inputs vehicle speed $V_s$, front wheel steering angled $\delta_{fs}$, lateral acceleration $(d^2y/dt^2)_s$ and yaw rate $(d\phi/dt)_s$ and calculates an actual yaw rate $(d\phi/dt)_O$ while actual vehicle behaviors are fed back. That is, the actual value estimating section 12 is an observer derived from the vehicle motion model. The actual yaw rate $(d\phi/dt)_O$ calculated in the actual value estimating section 12 is outputted to the Lissajou's figure processing section 13. The subscript "O" attached to the actual yaw rate $(d\phi/dt)_O$ denotes a parameter originated from the observer.

Figure 3:
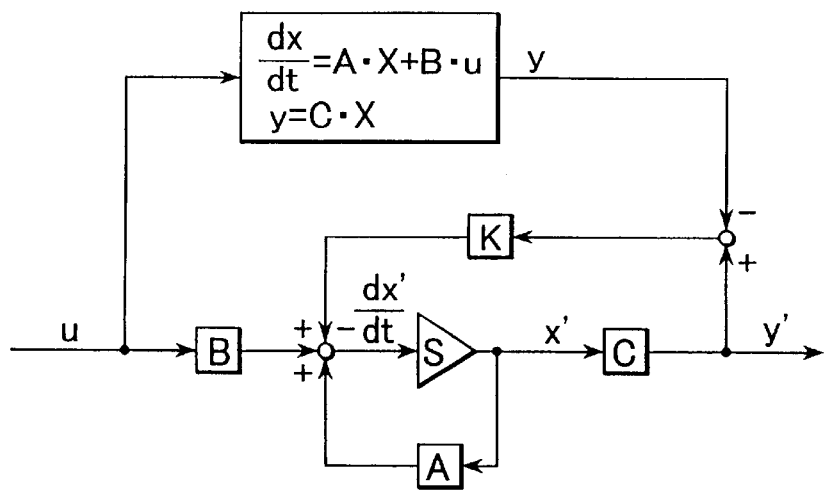
FIG. 3 is a circuit diagram showing a basic construction of an observer.

The construction of the observer according to this embodiment will be described by reference to FIG. 3.

When the output detected by the sensor is expressed as follows:

$$y(t) = C \cdot x(t) \quad (9)$$

The construction of the observer is:

$$(dx'(t)/dt) = (A - K \cdot C) \cdot x'(t) + K \cdot y(t) + B \cdot u(t) \quad (10)$$

where x(t) is state variable vector (superscript "'" indicates an estimating value); u(t) is input vector; A, B is coefficient matrix of state equation; y(t) is observable sensor output vector and is expressed as:

$$y(t) = [\beta_s (d\phi/dt)_s]^T$$

The vehicle slip angle $\beta_s$ detected by sensor is obtained by integrating the vehicle slip angular velocity $(d\beta/dt)_s$ detected by sensor. The vehicle slip angular velocity $(d\beta/dt)_s$ is obtained from the formula (3) based on the lateral acceleration $(d^2y/dt^2)_s$ detected by sensor and the yaw rate $(d\phi/dt)_s$ detected by sensor; C is matrix (in this embodiment, unit matrix) indicating the relationship between sensor output and state variable and K is feed-back gain matrix that can be arbitrarily established and C, K is expressed respectively as follows:

$$C = \begin{bmatrix} 1 & 0 \\ 0 & 1 \end{bmatrix}$$

$$K = \begin{bmatrix} k_{11} & k_{12} \\ k_{21} & k_{22} \end{bmatrix}$$

Hence, the actual yaw angular acceleration $(d^2\phi/dt^2)_0$ from the observer and the actual vehicle slip angular velocity $(d\beta/dt)_0$ are calculated by the following formulas (11) and (12):

$$(d^2\phi/dt^2)_0 = a_{11} \cdot (d\phi/dt)_0 + a_{12} \cdot \beta_0 + \quad (11)$$
$$b_{11} \cdot \delta_{fs} + k_{11} \cdot ((d\phi/dt)_s - (d\phi/dt)_0) + k_{12} \cdot (\beta_s - \beta_0)$$

$$(d\beta/dt)_0 = a_{21} \cdot (d\phi/dt)_0 + a_{22} \cdot \beta_0 + \quad (12)$$
$$k_{21} \cdot ((d\phi/dt)_s - (d\phi/dt)_0) + k_{22} \cdot (\beta_s - \beta_0)$$

Accordingly, an actual yaw rate $(d\phi/dt)_0$ and an actual vehicle slip angle $\beta_0$ are calculated by integrating thus calculated actual yaw angular acceleration $(d^2\phi/dt^2)_0$ and actual vehicle slip angular velocity $(d\beta/dt)_0$. Further, an actual front wheel slip angle $\beta_{f0}$ is calculated by substituting the actual vehicle slip angle $\beta_0$ and the actual yaw rate $(d\phi/dt)_0$ into the formula (6), respectively.

In the high friction coefficient road reference value estimating section 11 and the actual value estimating section 12, when the vehicle speed Vs=0, the calculation can not be performed due to the division by 0. Hence, when the vehicle travels at extremely low speeds, for example below 10 km/h, the yaw rate and the lateral acceleration are replaced with sensor values respectively. That is, $$(d\phi/dt)_H = (d\phi/dt)_L = (d\phi/dt)_0 = (d\phi/dt)_s$$

Further, the vehicle slip angle can be expressed from the geometric relationship of the turning on the stationary circle as:

$$\beta_H = \beta_L = \beta_0 = \delta_{fs} \cdot L_r/(L_f + L_r)$$

At this time, since no cornering force is generated, the front wheel slip angle is 0.

$$\beta_{fH} = \beta_{fL} = \beta_{f0} = 0$$

The Lissajou figure processing section 13 inputs vehicle speed $V_s$, lateral acceleration $(d^2y/dt^2)_s$, high friction coefficient road reference yaw rate $(d\phi/dt)_H$, high friction coefficient road reference yaw angular acceleration $(d^2\phi/dt^2)_H$, and actual yaw rate $(d\phi/dt)_0$ and forms a Lissajou's figure based on the high friction coefficient road reference yaw rate $(d\phi/dt)_H$ and the actual yaw rate $(d\phi/dt)_0$. Further, the Lissajou figure processing section 13 calculates a gradient r and an area S of the Lissajou's figure and outputs those to the road friction coefficient estimating section 14. Further, the Lissajou figure processing section 13 calculates a steering pattern variable $A\phi$ in integrating time $T_s$ which will be described hereinafter, further determines a maximum value $(d^2y/dt^2)_{max}$ of lateral acceleration sensor values $(d^2y/dt^2)_H$ in integrating time $T_s$ and outputs these steering pattern variable $A\phi$ and maximum value $(d^2y/dt^2)_{max}$ to the road friction coefficient estimating section 14.

Figure 4:
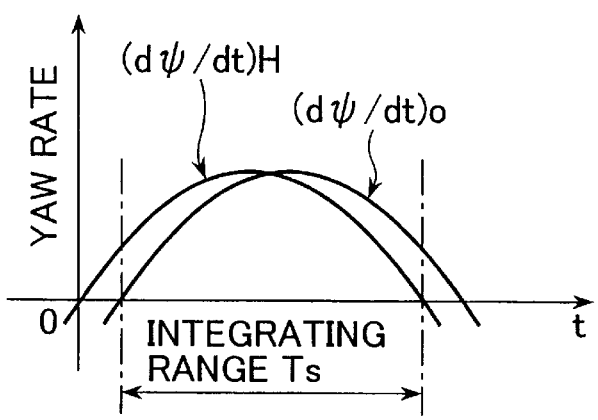
FIG. 4 is an explanatory view showing an integrating range.

The integrating time $T_s$ is defined as a time interval during which the high friction coefficient road reference yaw rate $(d\phi/dt)_H$ has the same sign as the actual yaw rate $(d\phi/dt)_0$ as shown in FIG. 4. Further, the gradient r is defined as a mean value of a ratio $r_i$ of high friction coefficient road reference yaw rate $(d\phi/dt)_H$ to actual yaw rate $(d\phi/dt)_0(r_i = (d\phi/dt)_H/(d\phi/dt)_0)$. That is, $$r = (1/n) \cdot \Sigma r_i \quad (13)$$

where n is a number of data in the integrating time $T_s$.

Figure 5:
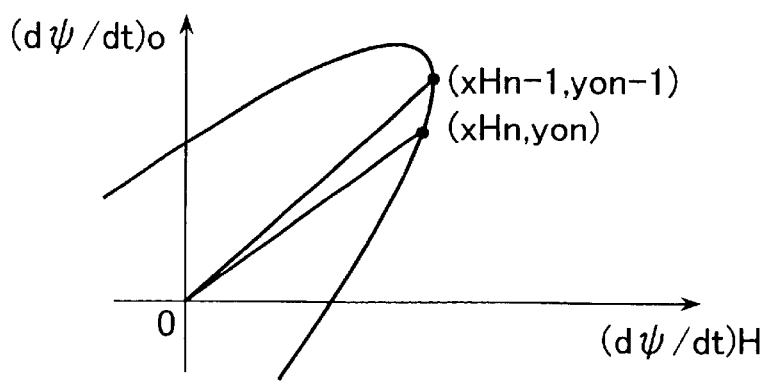
FIG. 5 is an explanatory view showing a calculation of an area of Lissajou's figure.

As shown in FIG. 5, the area S of Lissajou's figure is obtained by integrating small triangular areas. For example, letting a point $(x_{Hn-1}, y_{0n-1})$ be a value one cycle ($\Delta t = 10$ milliseconds) before a point $(x_{Hn}, y_{0n})$, a small triangular area $\Delta S_H$ is:

$$\Delta S_H = (\tfrac{1}{2}) \cdot |x_{Hn-1} \cdot (dy_{0n-1}/dt) - y_{0n-1} \cdot (dx_{Hn-1}/dt)| \cdot \Delta t \quad (14)$$

Figure 6:
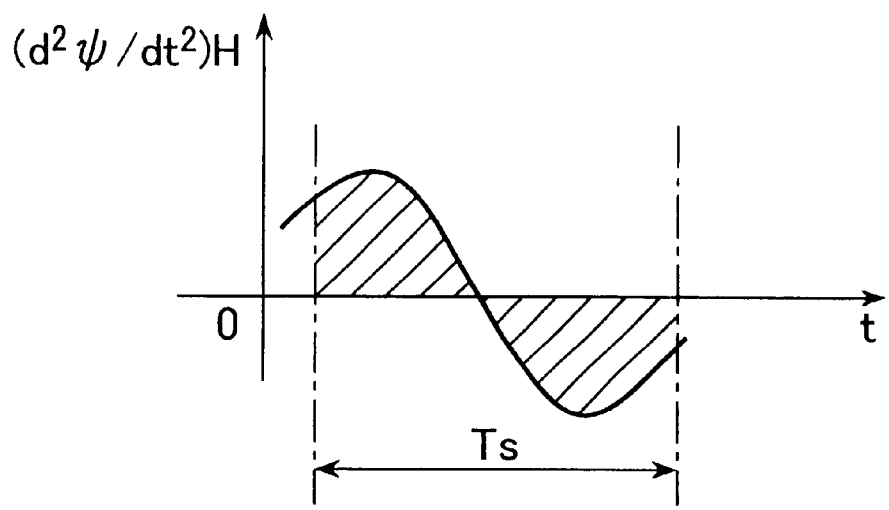
FIG. 6 is an explanatory view of a steering pattern variable.

The steering pattern variable $A\phi$ is a variable for indicating an emergency condition of the steering in integrating time $T_s$ and is calculated by the following formula (15):

$$\Delta A\phi = \int |(d^2\phi/dt^2)_H| dt \text{ (hatched line portion of FIG. 6) } \Delta A\phi = \Delta A\phi^2 \text{(15)}$$

The reason why $\Delta A\phi$ is squared is to nonlinearize $A\phi$.

The road friction coefficient estimating section 14 inputs gradient r of the Lissajou's figure, area S thereof. Steering pattern variable $A\phi$ and maximum value $(d^2y/dt^2)_{MAX}$ of lateral acceleration, estimates road friction coefficient and outputs it.

Specifically, in the road friction coefficient estimating section 14, the road friction coefficient is estimated by two methods according to the gradient r of a Lissajou's figure.

Figure 7:
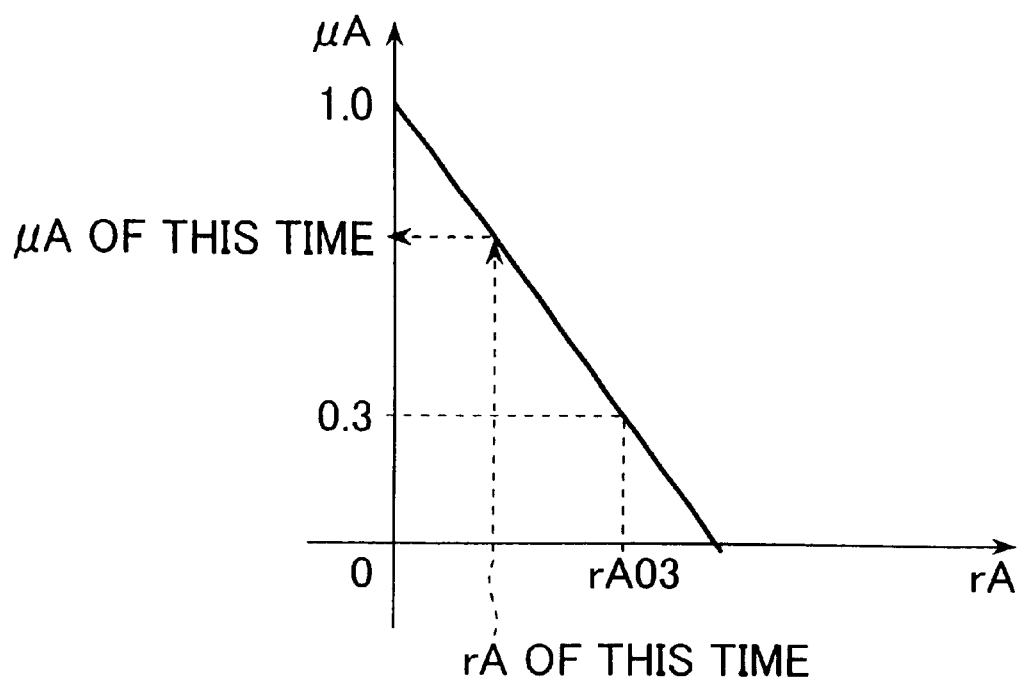
FIG. 7 is an explanatory view of a method of calculating a road friction coefficient estimating value $\mu_A$.

First, in case where the gradient of a Lissajou's figure is in the neighborhood of 45 degrees, for example, 0.8<r<1.2, a variable rA ($=S/A\phi$) is obtained from the steering pattern variable $A\phi$ and the area S of the Lissajou's figure. Then, an estimating value $\mu_A$ of the road friction coefficient of this time is calculated by comparing the variable rA of this time with a threshold value which has been experimentally determined beforehand for various road surfaces with different friction coefficients. In this embodiment of the present invention, as shown in FIG. 7, for example in case where the vehicle travels on a snowy frozen road and the variable rA is established to a variable rA03 (road friction coefficient= 0.3), an estimating value $\mu_A$ of road friction coefficient this time is:

$$\mu_A = -(0.7/rA03) \cdot rA + 1.0 \quad (16)$$

Further, in case where the gradient of the Lissajou's figure is in a range out of the neighborhood of 45 degrees (for example, r≦0.8 or r≧1.2), the value of lateral acceleration $(d^2y/dt^2)_{MAX}$ divided by gravitational acceleration is a road friction coefficient estimating value $\mu_y$.

Thus obtained road friction coefficient estimating values $\mu_A$ or $\mu_y$ is an output value $\mu_{out}$ out of the road friction coefficient estimating value. The Lissajou figure processing section 13 and the road friction coefficient estimating section 14 constitute a road friction coefficient estimating means.

The yaw rate has a small delay with respect to the steering input when the vehicle travels on a road surface with high friction coefficient and has a large delay with respect to the steering input when the vehicle travels on a road surface with low friction coefficient. Since it is difficult to calculate the delay in real time, an area S of a Lissajou's figure (the size of the area presents the delay between two waveforms as shown in FIGS. 8a and 8b) is obtained. Then, the road friction coefficient is estimated by comparing this area S with other area.

However, in case where the Lissajou's figure produces a change in both delay and size between two waveforms as shown in FIG. 8c, the gradient of the figure changes substantially (largely change from 45 degrees) and consequently the area differs from the one accompanied only by delay. Hence, when the effect of nonlinearity of tire is strong as shown in FIG. 9a, the Lissajou's figure of this moment changes in its gradient r and further the area S differs from the one having normal delay. As a result, it becomes difficult to estimate the road friction coefficient by comparing the area with other one.

Accordingly, first it is of importance to make a judgment from a gradient r of Lissajou's figure. That is, in case where the gradient of a Lissajou's figure is in the neighborhood of 45 degrees, it is judged that the tire is in a linear zone and therefore the road friction coefficient should be estimated based on an area S of the Lissajou's figure. On the other hand, in case where the gradient of a Lissajou's figure is in a range out of the neighborhood of 45 degrees, it is judged that the tire is in a nonlinear zone and therefore the road friction coefficient should be estimated based on a lateral acceleration $(d^2y/dt^2)_{MAX}$.

Further, generally the delay of yaw rate also changes according to driver's steering condition. That is, yaw rate tends to be delayed more, as a driver turns the steering wheel fast and tends to be delayed less, as the driver turns the steering wheel slowly. Taking notice of the pattern of delay of yaw rate with respect to the steering condition, an accurate estimation of road friction coefficient is available. Hence, in estimating road friction coefficient from the area S of Lissajou's figure, the emergency condition of steering is expressed as a steering pattern variable $A\phi$ obtained by squaring the integral of yaw angular acceleration $(d^2\phi/dt^2)_H$ and the variable $A\phi$ is used for estimating road friction coefficient.

Figure 10:
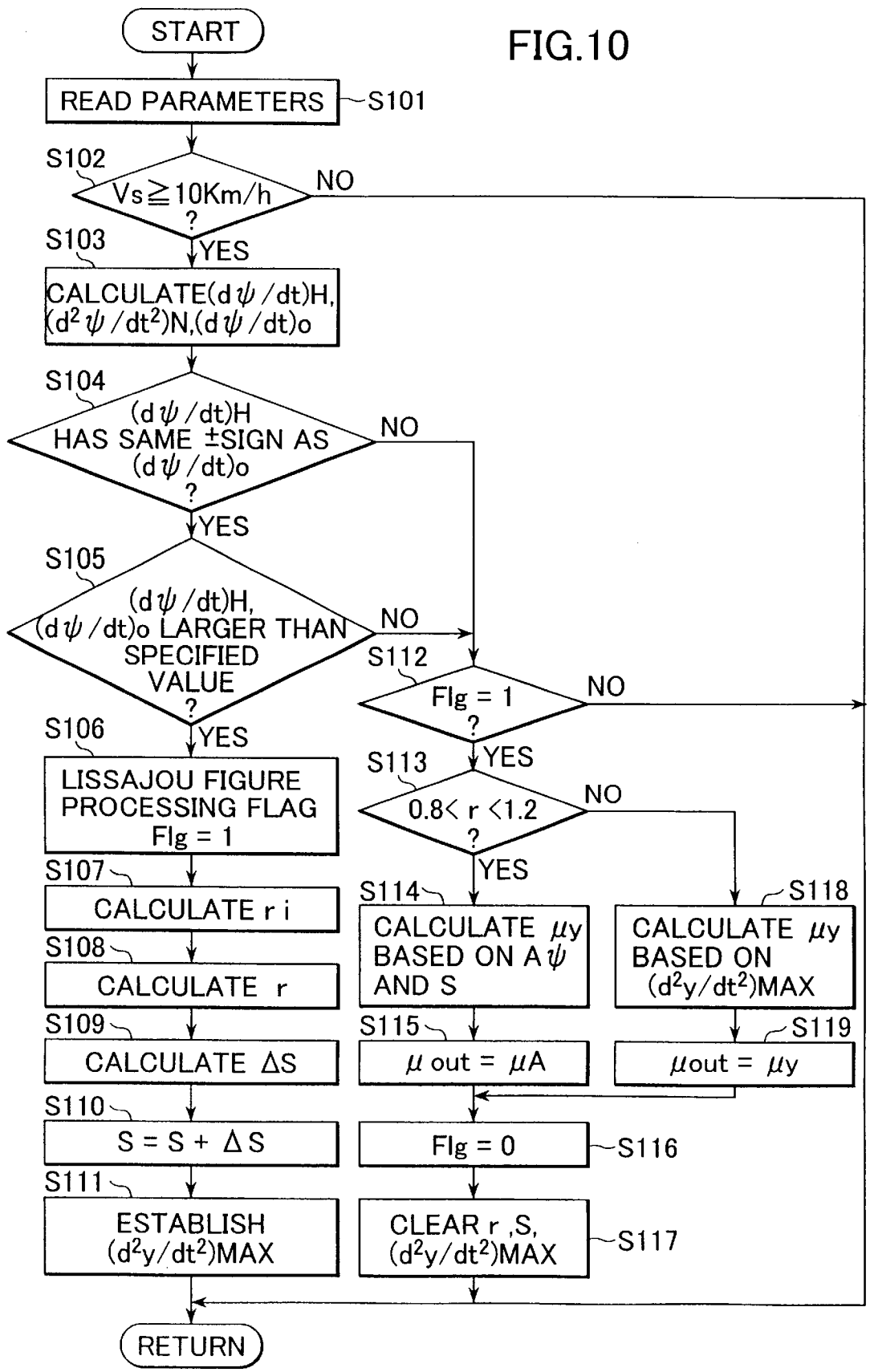
FIG. 10 is a flowchart showing steps for calculating a road friction coefficient estimating value according to an embodiment of the present invention.

Processes of estimating road friction coefficients will be described by reference to a flowchart of FIG. 10. This program is executed at a specified time interval (for example 10 milliseconds).

At a step (hereinafter referred to as S) 101, necessary parameters (sensor values) are read and the program goes to S102.

At S102, it is judged whether or not vehicle speed $V_s$ is larger than the lowest speed value where the vehicle motion model of the high friction coefficient reference value estimating section 11 and the actual value estimating section 12 can be applied, for example 10 km/h. As a result of this judgment, in case where the vehicle speed $V_s$ is larger than 10 km/h, the program goes to S103 where the high friction coefficient road reference yaw rate $(d\phi/dt)_H$ and the yaw angular acceleration $(d^2\phi/dt^2)_H$ are calculated in the high friction coefficient reference value estimating section 11 and the actual yaw rate $(d\phi/dt)_O$ is also calculated by the observer in the actual value estimating section 12. Further, as a result of the judgment at S102, in case where the vehicle speed $V_s$ is smaller than 10 km/h, the program leaves the routine.

Then, the program goes to S104 wherein it is judged whether or not the high friction coefficient road reference yaw rate $(d\phi/dt)_H$ and the actual yaw rate $(d\phi/dt)_O$ have the same sign and those are within the integrating time $T_s$.

As a result of this judgment, in case where it is judged that the high friction coefficient road reference yaw rate $(d\phi/dt)_H$ and the actual yaw rate $(d\phi/dt)_O$ have an identical sign and are within the integrating time $T_s$, the program goes to S105 where it is judged whether or not the high friction coefficient road reference yaw rate $(d\phi/dt)_H$ and the actual yaw rate $(d\phi/dt)_O$ are larger than a specified value, that is, whether or not the high friction coefficient road reference yaw rate $(d\phi/dt)_H$ and the actual yaw rate $(d\phi/dt)_O$ are in a range containing small errors.

As a result, in case where the high friction coefficient road reference yaw rate $(d\phi/dt)_H$ and the actual yaw rate $(d\phi/dt)_O$ are larger than the specified value, the program goes to S106 where a Lissajou figure processing flag $F_{lg}$ is set ($F_{lg}=1$).

Next, the program goes to S107 where a ratio $r_i$ of the actual yaw rate $(d\phi/dt)_O$ to the high friction coefficient road reference yaw rate $(d\phi/dt)_H (=(d\phi/dt)_O/(d\phi/dt)_H)$ is calculated and goes to S108 where a gradient r of Lissajou's figure is calculated based on the $r_i$ (accumulated since the integrating time starts) according to the formula (13).

After that, the program goes to S109 where a small triangular area $\Delta S_H$ of Lissajou's figure is calculated and then at S110, this area $\Delta S_H$ is added to the area S of Lissajou's figure which has been ever (since the integrating time starts) accumulated ($S=S+\Delta S_H$).

Then, the program goes to S111 where a maximum value $(d^2y/dt^2)_{MAX}$ of the inputted lateral acceleration sensor value $(d^2y/dt^2)_s$ is calculated and the program leaves the routine.

On the other hand, at S104, in case where the high friction coefficient road reference yaw rate $(d\phi/dt)_H$ and the actual yaw rate $(d\phi/dt)_O$ have an identical sign and are out of the integrating time $T_s$, or at S105, in case where either of the high friction coefficient road reference yaw rate $(d\phi/dt)_H$ and the actual yaw rate $(d\phi/dt)_O$ is smaller than a specified value and those are within a range of containing errors, the program goes to S112.

At S112, it is judged whether or not the Lissajou figure processing flag $F_{lg}$ is set, that is, whether or not the process has finished within the integrating time $T_s$. If the Lissajou figure processing flag $F_{lg}$ has been set and the process has finished within $T_s$, the program goes to S113. On the other hand, if the Lissajou figure processing flag $F_{lg}$ has not been set and the process has not yet finished within $T_s$, the program leaves the routine.

At S113, the gradient r of the Lissajou's figure is referred to and in case where the gradient r is in the neighborhood of 45 degrees, that is, in case of 0.8<r<1.2, it is judged that the tire is in a linear zone and the program goes to S114 where the steering pattern variable $A\phi$ is calculated based on the high friction coefficient road reference yaw angular acceleration $(d^2\phi/dt^2)_H$ according to the formula (15) and the road friction coefficient estimating value $\mu_A$ is calculated based on this steering pattern variable $A\phi$ and the area S of the Lissajou's figure according to the formula (16).

After that, the program goes to S115 where this road friction coefficient estimating value $\mu_A$ is established to a road friction coefficient estimating output value $\mu_{out}$ to be outputted from the control section 2 and goes to S116 where the Lissajou figure processing flag $F_{lg}$ is cleared ($F_{lg}=0$). Then, at S117, the gradient r and area S of the Lissajou's figure and the lateral acceleration maximum value $(d^2y/dt^2)_{MAX}$ that are stored for estimating a road friction coefficient this time, are cleared and the program leaves the routine.

On the other hand, as a result of the judgment of the gradient r of the Lissajou's figure at S113, in case where the gradient is away from the neighborhood of 45 degrees, that is, in case of $r \leq 0.8$ or $r \geq 1.2$, it is judged that the tire is in a nonlinear zone and the program goes to S118 in which a road friction coefficient estimating value $\mu_y$ is obtained by dividing the lateral acceleration maximum value $(d^2y/dt^2)_{MAX}$ by gravitational acceleration.

Then, the program goes to S119 where this road friction coefficient estimating value $\mu_y$ is established to a road friction coefficient estimating output value $\mu_{out}$ to be outputted from the control section 2 and goes to S116 where the Lissajou figure processing flag $F_{lg}$ is cleared ($F_{lg}=0$). Then, at S117, the gradient r and area S of the Lissajou's figure and the lateral acceleration maximum value $(d^2y/dt^2)_{MAX}$ that are stored for estimating a road friction coefficient this time, are cleared and the program leaves the routine.

Thus, according to the embodiment of the present invention, since a road friction coefficient can be estimated only by the outputs from the high friction coefficient road reference value estimating section 11 and the actual value estimating section 12, the road friction coefficients estimating apparatus has an advantage of that the construction of the apparatus is simple and the amount of calculation is small. Further, since in a linear zone of tire the road friction coefficient is estimated based on the change of the area S of Lissajou's figure and in a nonlinear zone of tire the road friction coefficient is estimated based on the lateral acceleration maximum value $(d^2y/dt^2)_{MAX}$, road friction coefficients can be estimated stably and accurately over a wide range of traveling condition. Further, since considering the degree of emergency of a vehicle driver the area S of Lissajou's figure is corrected by the steering pattern variable $A\phi$, a more accurate estimation of road friction coefficients can be performed.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A road friction coefficient estimating apparatus for a vehicle comprising:
   an actual value estimating means for estimating an actual value of a vehicle motion parameter;
   a high friction coefficient road reference value estimating means for estimating a high friction coefficient road reference value of said vehicle motion parameter based on a vehicle motion model when said vehicle travels on a road surface with high friction coefficient; and
   a road friction coefficient estimating means for forming a Lissajou's figure based on said actual value and said high friction coefficient road reference value and for estimating a road friction coefficient according to a gradient and an area of said Lissajou's figure.

2. The road friction coefficient estimating apparatus according to claim 1, wherein
   said road friction coefficient estimating means estimates said road friction coefficient based on said area of said Lissajou's figure when said gradient of said Lissajou's figure is in the neighborhood of 45 degrees.

3. The road friction coefficient estimating apparatus according to claim 2, wherein
   said area of said Lissajou's figure is corrected according to a degree of emergency of steering.

4. The road friction coefficient estimating apparatus according to claim 1, wherein
   said road friction coefficient estimating means estimates said road friction coefficient based on a lateral acceleration of said vehicle when said gradient of said Lissajou's figure is in a range out of the neighborhood of 45 degrees.

5. A road friction coefficient estimating apparatus for a vehicle comprising:
   an actual value estimating unit configured to estimate an actual value of a vehicle motion parameter including an actual yaw rate;
   a high friction coefficient road reference value estimating unit configured to estimate a high friction coefficient road reference value of said vehicle motion parameter based on a vehicle motion model when said vehicle travels on a road surface with high friction coefficient, said high friction coefficient road reference value including a high friction coefficient road reference yaw rate; and
   a road friction coefficient estimating unit configured to form a Lissajou's figure based on said actual yaw rate and said high friction coefficient road yaw rate, and to estimate a road friction coefficient according to a gradient and an area of said Lissajou's figure.

6. The estimator of claim 5, wherein said actual value comprises an actual yaw rate.

7. The estimator of claim 5, wherein said high friction coefficient road reference value comprises a high friction coefficient road reference yaw rate.

8. A road friction coefficient estimator, comprising:
   an actual value estimator that estimates an actual value of a vehicle motion parameter;
   only one friction coefficient road reference value estimator, wherein said friction coefficient road reference value estimator estimates a high friction coefficient road reference value of said vehicle motion parameter based on a vehicle motion model in accordance with a high friction coefficient; and
   a road friction coefficient estimator that estimates a road friction coefficient based upon said actual value and said friction coefficient road reference value.

9. The estimator of claim 8, wherein said road friction coefficient estimator forms a Lissajous figure.

10. The estimator of claim 9, wherein said Lissajous figure is based on said actual value.

11. The estimator of claim 9, wherein said Lissajous figure is based on said high friction coefficient road reference value.

12. The estimator of claim 9, wherein said road friction coefficient estimator estimates said road friction coefficient based upon a gradient of said Lissajous figure.

13. The estimator of claim 9, wherein said road friction coefficient estimator estimates said road friction coefficient based upon an area of said Lissajous figure.

* * * * *